United States Patent [19]
Pistay

[11] Patent Number: 5,344,437
[45] Date of Patent: Sep. 6, 1994

[54] MASSAGING THERAPEUTIC PILLOW WITH REMOVABLE ICE PACK

[75] Inventor: George R. Pistay, Los Angeles, Calif.

[73] Assignee: Sub I.P., Inc., Glendale, Calif.

[21] Appl. No.: 59,409

[22] Filed: May 10, 1993

[51] Int. Cl.$^5$ .................................. A61F 7/00
[52] U.S. Cl. .................... 607/109; 607/114; 601/58
[58] Field of Search .............. 607/96, 104, 108–110, 607/114; 128/32; 5/421, 636, 640, 644–645, 441–442

[56] References Cited

U.S. PATENT DOCUMENTS

| | | | |
|---|---|---|---|
| 2,298,299 | 10/1942 | Joy et al. | 607/111 X |
| 3,323,517 | 6/1967 | Keller | 607/109 X |
| 4,858,259 | 8/1989 | Simmons et al. | 607/114 X |
| 4,887,326 | 12/1989 | O'Brien et al. | 607/114 X |
| 5,257,429 | 11/1993 | Genis | 607/114 X |

*Primary Examiner*—Angela D. Sykes
*Attorney, Agent, or Firm*—David O'Reilly

[57] ABSTRACT

A therapeutic massaging pillow that is versatile in construction and use. The pillow is provided in a U-shaped form having extensions that fit around the neck and a thicker upper portion that is in intimate contact with the posterior portion of the head of a person using the pillow. The pillow provides a pocket on one or both sides for receiving a container that is filled with a material that can be heated or cooled. Additionally a cavity at the thickest upper portion of the pillow is provided for installing an electrically operated vibrator. The vibrator is embedded in a foam housing and has a switch that is easily accessible through the foam material. Batteries at each end of the housing are provided to operate the vibrating mechanism. The pillow is versatile in construction and use by allowing application of hot or cold temperatures to the posterior of the head through a fluid filled container inserted in the pocket or separately applying a massaging effect of the vibrator.

6 Claims, 1 Drawing Sheet

MASSAGING THERAPEUTIC PILLOW WITH REMOVABLE ICE PACK

FIELD OF THE INVENTION

This invention relates to a therapeutic pillow for treatment of headaches and more particularly relates to a therapeutic pillow having a removable ice pack which also includes a massaging device.

BACKGROUND OF THE INVENTION

There are devices available for treating headaches more particularly there is a pillow available for treating headaches with a therapeutic ice pack that fits in the pocket of a pillow. This device can provide hot or cold treatment so that the therapeutic effect of hot and cold treatment can be applied directly to the sub occipital area of the head.

One such device is disclosed and described in U.S. Pat. Nos. 4,783,866 and 4,858,259 owned by the same entity as this application. In this device a U-shaped therapeutic pillow is provided with a pocket for receiving a container containing a material that can be heated or cooled for application to the occipital area of the head. The therapeutic pillow is in a U-shape configuration having extensions that fit around the neck with the upper portion of the pillow applying the soothing treatment. This device is very effective in the treatment of headaches and in particular can be useful in treating migraine headaches.

It is also known that mechanical stimulation of various areas of the body can provide relief from the pain of sore muscles and tension. For example there are devices that include a vibrating massaging apparatus that can be wrapped around the neck to provide a massaging effect to the neck. One such device on the market provides a velcro closure to wrap the device around the neck like a collar or scarf.

It would be advantageous if such massaging action could be applied to the posterior or occipital region of the head to provide a soothing, stimulating effect to relieve tension or migrane headaches.

It is therefore one object of the present invention to provide a therapeutic pillow that includes the ability to apply hot or cold treatment to the occipital area of the head and/or also apply a massaging action.

Yet another object of the present invention is to provide a therapeutic pillow that includes the ability to apply hot and cold ice packs that also includes a vibrating stimulating device in a pocket at the upper portion of the pillow.

Another object of the present invention is to provide a therapeutic pillow having the ability to apply hot or cold ice packs which has a therapeutic massaging device that fits in a pocket in an upper portion of the pillow for application of stimulating massage to the posterior area of the head.

Still another object of the present invention is to provide a therapeutic pillow having a stimulating massaging device operated by batteries.

Yet another object of the present invention is to provide a therapeutic pillow having a massaging stimulating device that allows the batteries in the device to be easily removed and replaced.

BRIEF DESCRIPTION OF THE INVENTION

The purpose of the present invention is to provide a specially contoured pillow having a covering for receiving a container that can be inserted or removed from the pillow. The sealed container is filled with a material that can be heated or cooled for application to the occipital area of the head when installed in the pillow. It is also desired to add a stimulating massaging effect of a vibration device to the therapeutic pillow to be used with or without the hot or cold treatment.

The purposes of the present invention are achieved by providing a pillow contoured to fit around a neck having a portion shaped to apply an even force to a posterior portion of the skull when a person's head is resting on the pillow. The pillow has a substantial U-shape with extensions that fit around the neck area allowing the head to rest on the upper portion. The pillow is filled with a suitable polyester material, a foam material, or soft material and includes a pocket shaped to receive a container filled with a material that can be heated or cooled.

The temperature retaining fluid is preferably a material such as those disclosed in U.S. Pat. Nos. 2,803,115 and 3,545,230 incorporated herein by reference. These devices disclose a slurry or insoluble hydrophylic gel which can be frozen and molded into various geometric shapes. They are particularly useful because they retain the particular configuration as long as the material remains substantially rigid. One of these materials is sometimes know by the trademark "BLUE-ICE". Other materials are available which can be used but it is preferably and desired that the material be sufficiently pliant when cold to conform to the shape of the posterior or occipital region of the head of a person lying on a specially contoured pillow.

A covering over a substantial portion of one side of the pillow provides a pocket for receiving a container or containers filled with the temperature retaining fluid. The interior portion of the pocket for receiving the temperature retaining pillow is preferably lined with a moisture proof material to prevent condensation from soaking through to the surface of the pillow. The pocket may then be closed with a suitable closure such as snaps or hook-loop material such as that sold under the trademark of "VELCRO" sewn to the pillow and a pocket flap.

To provide the effect of a stimulating massage, a cavity is formed at the upper rear portion of the pillow that extends into the center of the pillow stuffing or filling. A vibrating massaging device is inserted in this pocket which is then closed with a zipper. An on-off switch on the vibrating stimulating device can be easily operated through the cloth material of the pillow.

Preferably the vibrating stimulating device is mounted in a soft foam enclosure having three compartments. A central compartment surrounds the vibrator, while compartments on the outer ends of the soft foam enclosure are constructed to receive the batteries for operating the vibrator. The outer compartments are open on their ends to allow the batteries to be easily removed and replaced.

To provide a stimulating massage the soft foam housings with the vibrator and batteries installed is inserted in the cavity at the upper portion of the pillow. The switch at the upper end of the pillow may then be operated to start the vibrating device. This can be done either before or after the cavity is closed by drawing the zipper closure. The pillow is then placed on the back of the head with the extensions around the neck. When a person lies on the pillow, the vibrator provides a stimulating massage to the posterior of the head to provide soothing, comfortable relief for tension or migrane headaches.

The pillow can also be used with or without the hot or cold treatment. If the cold treatment is to be used, a container having the temperature retaining material is cooled or heated and inserted in the pocket of the pillow. A patient then can lay or otherwise rest his head on the pillow with the extension partially extended around the posterior portion of the neck and the occipital region of the head in intimate contact with the area covered by the cold or hot pack.

The effect of the treatment to the posterior of the head in intimate contact with the occipital region of the head decreases the metabolism of the muscles thereby decreasing spasm. The vibrator can provide a stimulating, relaxing effect to the head. Thus the pillow can be effectively used to treat headache pain and particularly treat migraine and muscle contraction headaches which are two different kinds of headaches sharing the same physiological patho-physiological changes. With a migraine headache there is dilation of arteries and muscle contraction, while in the muscle contraction headaches there is only muscle contraction. The vibrating stimulating massage of course should be more effective in the type of headache where there is muscle contraction because the massaging effect of the vibrator will help to relieve tension and relax the muscle contractions. If preferred hot or cold temperature application can be provided with the vibrating massage used before or afterwards or if desired at the same time. The results of the application of the temperature and massaging pillow to headaches both migraine and muscle contraction headaches produces relief which is as good or better than analgesics.

The above and other features of this invention will be fully understood from the following detailed description and the accompanying drawings, in which:

DETAILED DESCRIPTION OF THE INVENTION

Figure 1:
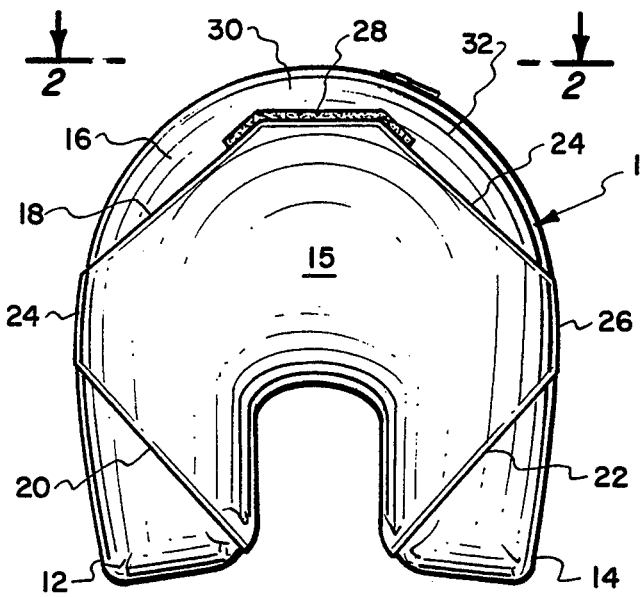
FIG. 1 is a top view of a therapeutic massaging pillow constructed according to the invention.

The therapeutic massaging pillow illustrated in FIG. 1 is for the purpose of headache management and treatment which was not convenient with prior therapeutic packs. The pillow shown generally at 10 has extensions 12 and 14 which are contoured to fit around the posterior portion of the neck to bring the surface area 16 into close intimate contact with posterior or occipital region of the head.

The surface area 16 of pillow 10 is covered with a soft cloth material 18 bounded at 18, 20, 22, and 24 to form a pocket 25 (FIG. 3) for receiving a container filled with a temperature retaining fluid. The soft cloth material 15 is stitched at boundaries 20 and 22 and at the edges of the pillow along sides 24 and 26. Boundaries 18 and 24 are left free to provide an entrance to pocket 25 formed by the cloth material 15.

A suitable closure 28 is provided comprised preferably of a non-bulky hook and loop clasp material such as "VELCRO." The U-shape therapeutic massage pillow has upper thicker portion 30 and thinner neck portion formed by extensions 12 and 14. The therapeutic pillow for treatment with hot or cold packs is shown and described generally in U.S. Pat. Nos. 4,783,886 and 4,858,259 incorporated herein by reference.

Pillow 10 has thicker head portion 30 and tapers toward neck portion formed by extensions 12 and 14. Pocket 25 provides a receptacle for receiving flexible plastic containers (not shown) that may be filled with a temperature retaining material such as "BLUE ICE" described above. The entire pillow is covered with a soft, durable material 32 and has a soft polyester fluffing filling 34 such as down or a non-allergenic foam material.

Figure 3:
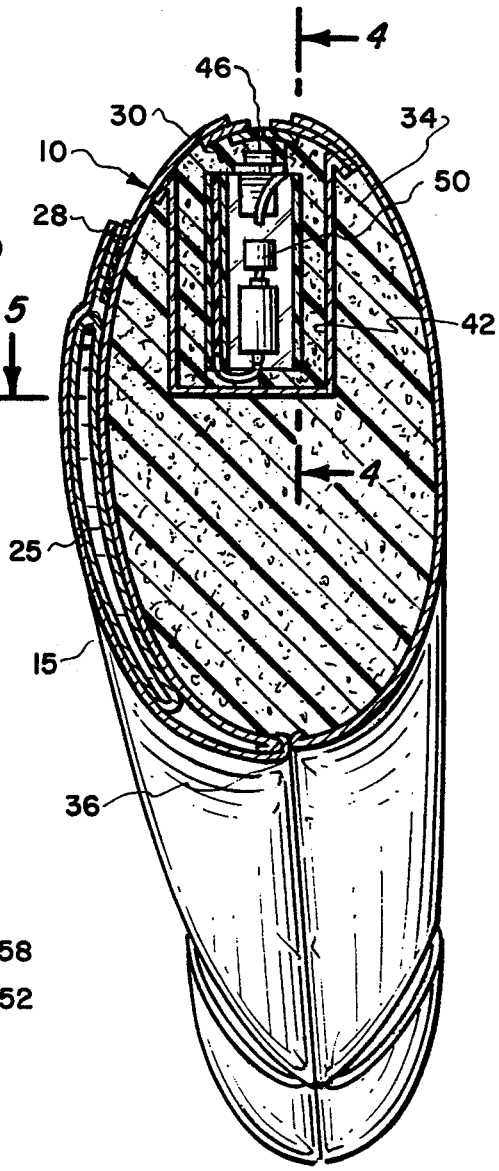
FIG. 3 is a sectional view taken at 3—3 of FIG. 2.

Material 15 covering the surface of pillow 10 forming pocket 25 also preferably has a lining of moisture-proof material to prevent condensation from soaking through the surface of the pillow when a therapeutic pack is installed in pocket 25. A moisture resistant material such as "THERAFOAM" suede would be suitable. This material is comprised of 50% cotton and 50% polyester. As can be seen in FIG. 3, pillow 10 is thicker at the upper end 30 and tapers toward neck extensions 12 and 14. Material 15 forming pocket 25 is sewn into seams 36 on each side to provide a covering over substantially the entire surface 16 of pillow 10.

Figure 2:
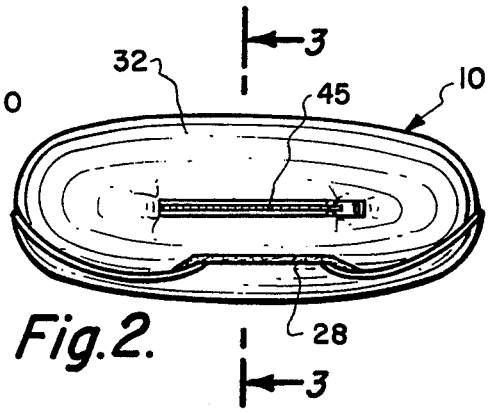
FIG. 2 is a view of the upper end of the therapeutic massaging pillow taken at 2—2 of FIG. 1.
Figure 4:
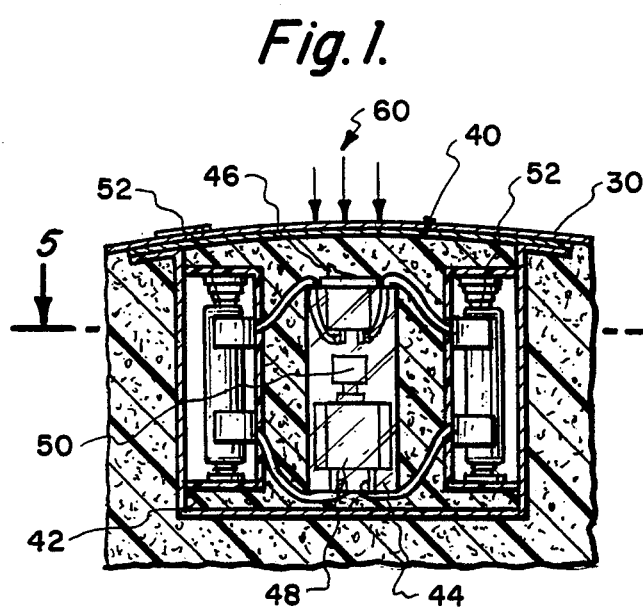
FIG. 4 is a sectional view illustrating the massaging device taken at 4—4 of FIG. 3.
Figure 5:
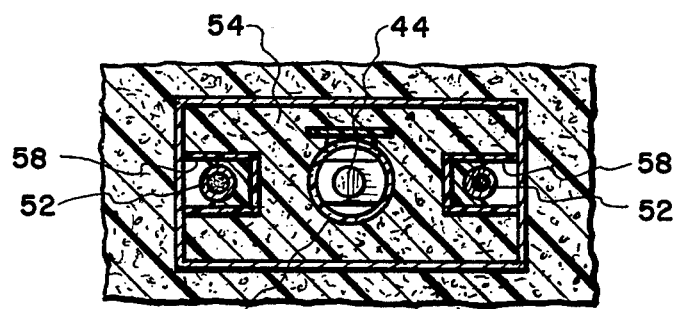
FIG. 5 is a sectional view taken at 5—5 of FIG. 4.

The pillow as described is very effective in providing hot or cold applications to the occipital region of the head to relieve migraine or muscle contraction headaches. It is also desirable to enhance the effect of the pillow by providing a soothing massage to the posterior area of the head. To provide the massaging action, a vibrating apparatus 40 may be inserted at the upper end 30 of pillow 10 in a cavity 42 formed in the foam filling 34. The cavity is closed by a zipper 46 as shown in FIG. 2.

Vibrating massaging device 40 is comprised of a small cylindrical vibrator 44, readily available. Vibrator 44 has an on-off switch 46 and a small motor 48 that drives an eccentric weight 50.

Power is provided for vibrator 44 by two one and one half volt (1½ V) batteries 52 mounted in compartments on either side of vibrator 44. A housing 54 for vibrator 44 and batteries 52 is provided by a resilient foam material completely surrounding vibrator 44 to provide a resilient padding to separate the massaging device and cushion the hard surfaces. Cavity 42 extends well into the foam material 34 providing the cushioning for the pillow such that a head resting on the pillow can be treated with the massaging effects of vibrator 44. Cavity 42 is provided by a material similar to that used to cover pillow 10. Foam material 54 forming the housing for the vibrator 44 and batteries 52 comfortable fits in cavity 42 through zipper 46. Thus the entire vibration massaging assembly 40 can be removed from cavity 42 for easy replacement of batteries 52.

Foam housing 54 for vibrator 44 and batteries 52 is constructed to ease replacement of the batteries. For that reason vibrator 44 is centrally embedded in a compartment 56 in foam housing 54 while batteries 52 are installed in open ended compartments 58 at either end of foam housing 54. This permits the batteries to be easily replaced when the entire vibrating assembly 40 is lifted from cavity 42 through opening 46.

Although not shown it should be clear that material 15 forming pocket 25 could be provided on both sides of pillow 10 so that a temperature retaining fluid filled container can be used on either side of the pillow. Also with vibrating massaging assembly 40 placed centrally deep into the foam filling 34 of the pillow the massaging action can be provided from either side of the pillow.

In use the pillow is placed with extension 12 and 14 around the neck and the upper portion 30 of the pillow abutting the posterior portion of the head. Vibrator 44 can be turned on by switch 46 which can be manipulated by pressing down on the upper end 30 of the pillow as indicated by arrows 60 activating rocker switch 46. This activates rocker switch 46 and turns on vibrator 44 providing a soothing massaging action to the posterior area of the head.

If desired a liquid filled cold or hot pack can be placed in pocket 25 and used in conjunction with the massaging action of vibrator 44. However preferably they would be used independently. The versatility of the pillow is the ability to apply hot and cold temperatures to the effected area or to apply a soothing massaging action or both. One can be used completely independent of the other without having to provide a separate pillow for each.

Thus there has been disclosed a unique therapeutic massaging pillow that is versatile and effective in use. The pillow provides a construction that allows a therapeutic hot or cold pack to be applied to affected areas of the head to treat headaches. The pillow also provides a vibrating device that can be used alone or in conjunction with the application of the cold pack. The vibrating device is easily operated and is constructed in a manner that allows user to easily change the batteries by removing the vibrating assembly from a cavity in the foam filling of the pillow.

This invention is not to be limited by the embodiment shown in the drawings and described in the description which is given by way of example and not of limitation, but only in accordance with the scope of the appended claims.

What is claimed is:

1. A therapy pillow for treating headaches comprising;
   a U-shaped cushioned pillow fitted with a soft resilient material, said U-shaped cushioned pillow having a head end and a pair of extensions for fitting around the neck of a person undergoing treatment;
   pocket means formed on at least one side of said pillow and extending to near the end of said extensions; said pocket means being constructed to receive a removable cooling or heating insert;
   said pocket means being constructed to provide intimate contact over a substantial portion of the occupational region of a human head resting on said U-shaped cushioned pillow with said extension fitted around the neck;
   said pocket means having an opening at said head end of said U-shaped cushioned pillow for removably inserting said cooling or heating insert;
   closure means for closing and securing said pocket means to secure said cooling or heating insert in said pocket means;
   a cavity formed in said head end of said U-shaped cushioned pillow;
   vibrating means inserted into said cavity in said head end of said U-shaped cushioned pillow;
   activating means for activation of said vibration means from outside said U-shaped cushioned pillow for massaging a posterior portion of a head resting on said head end of said U-shaped cushioned pillow with said vibrating means;
   whereby said U-shaped cushioned pillow can massage, heat or cool together, or independently for effective treatment of headaches.

2. The therapy pillow, according to claim 1 wherein said vibrating means comprises battery operated vibrating means; a resilient housing for said vibrating means to further cushion said vibrating means; said cavity in said head end of said U-shaped cushioned pillow being constructed to allow said vibrating means to be removed for replacement of said batteries.

3. The therapy pillow according to claim 2 in which said resilient housing for said vibrating means is constructed to house said vibrating means with said batteries easily accessible for removal and replacement.

4. The therapy pillow according to claim 3 in which said resilient housing is formed with a central compartment and a pair of open ended compartments on opposite sides of said central compartment; a vibrator being sealed in said central compartment; said batteries being mounted in said open ended compartments for easy removal and replacement when said resilient housing with said vibrating means is removed from said compartment.

5. The therapy pillow according to claim 4 in which said activating means comprises a switch on the end of said vibrator; said switch being exposed at one end of said resilient housing when said vibrator is sealed in said central compartment; said resilient housing fitting in said cavity with said switch at an open end of said cavity for easy access by a patient being treated whereby the vibrator may be easily turned on and off.

6. The therapy pillow according to claim 5 including a zipper for closing said cavity; said resilient housing positioning said vibrating means in said cavity with said switch beneath said zipper for easy access and operation.

* * * * *